Figure 1:
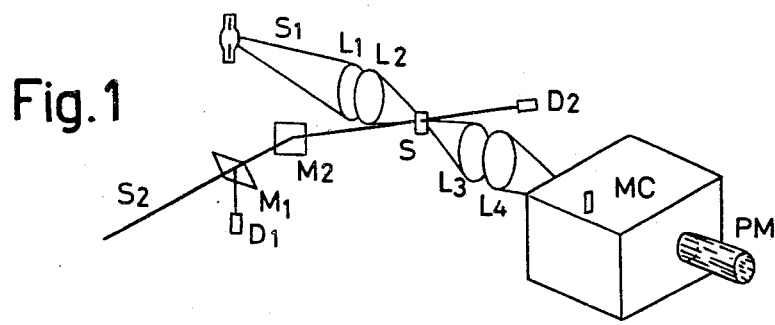

United States Patent [19]

Giannini et al.

[11] 4,376,820

[45] Mar. 15, 1983

[54] COMPOSITION SUITABLE FOR TESTING BIOLOGICAL TISSUES AND/OR LIQUIDS, AND THE METHOD OF USE

[75] Inventors: Ivo Giannini; Vittorio Baroncelli, both of Rome, Italy

[73] Assignee: E.N.I. Ente Nazionale Idrocarburi, Rome, Italy

[21] Appl. No.: 351,582

[22] Filed: Feb. 23, 1982

Related U.S. Application Data

[62] Division of Ser. No. 165,787, Jul. 3, 1980, Pat. No. 4,331,759.

[30] Foreign Application Priority Data

Sep. 10, 1979 [IT] Italy .................. 25568 A/79

[51] Int. Cl.³ ........................................... G01N 33/50
[52] U.S. Cl. .................................. 435/4; 435/6; 435/29; 435/527; 424/7.1
[58] Field of Search ............... 435/29, 34, 255, 4, 435/6; 424/7, 2; 252/408, 301.16, 301.25, 301.26; 23/932, 927, 915, 230 B; 250/345

[56] References Cited

U.S. PATENT DOCUMENTS

| | | | |
|---|---|---|---|
| 3,016,292 | 1/1962 | Bauer et al. | 23/932 X |
| 3,298,789 | 1/1967 | Mast | 23/230 B X |
| 3,682,783 | 8/1972 | Dahms et al. | 252/408 X |
| 4,094,745 | 6/1978 | Scholefield | 435/34 X |
| 4,174,384 | 11/1979 | Ullman et al. | 424/7 X |
| 4,207,469 | 6/1980 | Hopkins et al. | 250/345 X |
| 4,219,337 | 8/1980 | Grossberg et al. | 252/408 X |
| 4,225,669 | 9/1980 | Melnick et al. | 435/34 X |
| 4,225,783 | 9/1980 | Palin et al. | 435/29 X |
| 4,233,402 | 11/1980 | Maggio et al. | 424/7 X |
| 4,252,783 | 2/1981 | Kam et al. | 424/7 X |
| 4,336,029 | 6/1982 | Mabale | 23/230 B |
| 4,337,063 | 6/1982 | Mihara et al. | 23/230 B |

*Primary Examiner*—Kenneth M. Schor
*Attorney, Agent, or Firm*—Morgan, Finnegan, Pine, Foley & Lee

[57] ABSTRACT

The invention relates to a composition suitable for testing biological tissues and/or liquids, the composition consisting of:

(a) a dye chosen from the xanthene, azine, oxazine or acridine series, or from water-soluble dyes of the "diazo" series, or triphenylmethane,
(b) a medium compatible with the biological tissue and/or liquid,
(c) a substance capable of rapidly de-energizing the dye molecules when it encounters them (i.e. a quencher).

The test method using said composition is also described.

1 Claim, 7 Drawing Figures

COMPOSITION SUITABLE FOR TESTING BIOLOGICAL TISSUES AND/OR LIQUIDS, AND THE METHOD OF USE

This is a division of application Ser. No. 165,787, filed July 3, 1980, now U.S. Pat. No. 4,331,759.

This invention relates to a special composition suitable for testing biological tissues and/or liquids, i.e. for checking the presence of particular constituents in them. It also relates to the test method using said composition. For complete understanding of the subject matter and objects of the present invention, it is advantageous to consider certain general concepts which constitute the theoretical support for the subject under consideration.

When a substance absorbs visible or ultraviolet light, it is known that an electron contained therein passes from its basic state to an excited "singlet" state.

Intersystem crossing can then take place, with the creation of metastable "triplet" state in which the electron remains trapped until de-energising takes place by a quenching reaction (by encounter with another molecule) or by light emission (phosphorescence), or by other processes, all of which are relatively slow.

These phenomena are easily determined in various categories of natural and synthetic dyes.

One method widely used for studying and quantitatively determining these phenomena is the so-called flash photolysis method, in which the sample containing the substance to be studied is subjected to the radiation of a pulse light source (flash) which puts a discrete number of coloured molecules into the excited electron state.

The development of the aforesaid processes is observed by detecting the absorption of a continuous monochromatic light beam by the sample, this being recorded against time by a suitable electronic device (oscilloscope etc.).

This type of method has undergone considerable qualitative progress during recent years, in terms of a higher sensitivity, obtainable by using pulsed lasers as the disturbance source.

It is not known to use methods of the above type for studying and characterising biological tissues and/or liquids, with the notable exception of the case in which the tissue under examination contains a large quantity of a photosensitive natural substance, as in the case of the pigments of chlorophyll photosynthesis, rhodopsin and carboxyhaemoglobin.

In this respect, in the case of a tissue which is only lightly coloured, the flash light preferentially undergoes diffusion processes rather than absorption. However, the tissue can be dyed with synthetic dyes as is usual in optical microscope observation methods. In this respect, the fact that the dye succeeds in dyeing a tissue signifies that it becomes bonded to it in some manner.

However, there are at least two basic difficulties in using flash photolysis techniques in this context, in samples with strong diffusion effects.

Firstly, as the bonded dye concentrations are rather low, it has been doubtful whether significant signals could be obtained using this method. Secondly, it was not previously predictable that signals originating from absorptions characteristic of the metastable states of the dye would be different in the case of a dye bonded to a particular tissue from those originating from molecules in solution or bonded differently.

It has now been surprisingly found possible to overcome both these difficulties by preparing adductions of the constituent of the biological tissue and/or liquid concerned, with a dye which is synthetic or at least not present in physiological fluids or solutions, by bringing into contact a sample to be examined with a composition which constitutes the first subject matter of the invention, and which is constituted by the dye, a medium compatible with the biological tissue and/or liquid, and a substance capable of de-energising the dye molecules when it encounters them (quencher).

As stated, the composition which forms the adduction with the physiological constituent is formed by (a) a dye chosen from the azine, oxazine, acridine or xanthene series, or from certain water-soluble dyes of the "diazo" series, or triphenylmethane; (b) a medium compatible with the physiological constituent, and constituted by an aqueous solution containing various salts such as NaCl, $CaCl_2$ and the like in a concentration such as to be approximately isotonic with the physiological component (0.1–1% by weight), and other components in smaller proportion such as glucose, buffer mixtures etc., added so as to condition the vitality of the cells present, the pH of the medium being able to vary to a certain extent about neutrality (from pH 4.5 to pH 9.5), and small quantities of organic solvents being able to be added in order to increase the dye solubility; and (c) a quencher (i.e. which causes rapid de-energising of the dye molecules when the two molecules encounter each other), which can be potassium (or sodium) iodide (from $10^{-2}$ to 0.2 M), or the salt of a paramagnetic transition metal (from $10^{-2}$ to 0.2 M of Co, Fe, Ni, chosen in the form of $CoCl_2$ or the like), possibly in the presence of a chelating substance such as tetracetic ethylenediamino acid (EDTA); or finally the quencher used can be a defined quantity of molecular oxygen ($O_2$) dissolved in water (for example by saturating the sample solution with $O_2$ at a determined temperature).

The composition stated heretofore is used for carrying out a test method for biological tissues and/or liquids, which in its turn constitutes the second subject matter of the present invention.

This method consists of initially treating the sample of substance to be examined with the composition, subjecting the resultant substance to radiation by a first ray of pulse light, traversing the sample thus treated with a second ray of monochromatic light, and analysing the exit optical intensity of this latter as a function of time.

It has been found in this manner that the signals originating from the absorption of metastable states of dye molecules bonded into the cells to be examined are distinctly different in amplitude and/or time variation from those originating from the molecules in solution or from other cells.

The method thus succeeds in characterising the individual cells present in the tissue.

This method has been found particularly suitable for testing fermenting cell cultures, in distinguishing the dead cells from the live cells, and the yeast cells from the bacteria cells; and in the quantitative analysis of blood leucocytes. The method is able on the one hand to provide automatic measurements (taking just a few seconds) as a replacement for long and bothersome routine procedures necessary in the case of the optical microscope. It can also succeed in displaying characteristics undistinguishable to the eye, relative to the specific molecular interaction of the dye with some of the cell constituents.

It can therefore be used for tests which at the present time cannot be carried out, or are possible only using much more complicated methods. In particular, it is easy to forecast its use in tumour diagnosis because of the possibility for quantitatively determining the DNA-dye interaction.

FIG. 1 is a diagrammatic representation, by way of non-limiting example, of the apparatus used by us in these tests.

$S_1$ is the mercury lamp, and $S_2$ is the laser beam. $L_1$, $L_2$, $L_3$, $L_4$ are quartz lenses. $M_1$, $M_2$ are mirrors, and $D_1$, $D_2$ are solid state detectors which detect the laser pulse. MC is the high luminosity monochromator. S indicates the position of the sample, and PM is the photomultiplier. Filters and irises are omitted for clarity.

The pulsated light beam was obtained from a Nd laser, namely a commercial YAG (Chromatix mod. 1000) which emits light pulses of 0.1–0.5 mJ of about 150 ns in length, and with a repetition frequency of about 50 Hz.

The laser colour is variable from blue ($\lambda = 473$ nm) to near infrared. The observation beam was produced by a suitably filtered high pressure mercury lamp. Both the beams were focused into a zone of the sample of about 0.2 mm diameter, such that an angle of about 15° was formed between them. The sample cell was 2 mm thick. The light from the lamp passed through a large aperture monochromator, and was fed to a photomultiplier ,Philips XP1113). The electrical output of the photomultiplier was recorded continuously as the average value, and was also fed to a preamplifier with a pass band between 0.5 KHz and 30 MHz and then amplified, recorded on digital memories, and stored in a small computer (LABEN 70).

The signal obtained from a single pulse was recorded and added to that from hundreds of analogous pulses. Thus a signal average was obtained in which the noise was reduced by a factor of more than 10 relative to the signal originating from a single pulse. As the repetition frequency of the pulses was relatively high, the result of the measurements was obtained in just a few seconds. The storage in the computer made reproduction and processing of the signal possible, using magnetic tape, plotters etc.

The stored signal contains a considerable quantity of data, such as the amplitude of the absorption at various observation wavelengths, and its variation with time.

If this amplitude is $V(\lambda, t)$, it is generally possible to fix $\lambda$ and $t$ such that:

$$V(\lambda_o, t_o) = k_1 + k_2 n_c$$

where $n_c$ is the number of cells relevant to our purpose, and $k_1$ and $k_2$ are constants obtainable by a calibration process, i.e. by introducing a sample of known composition into the apparatus.

EXAMPLE 1

Testing of cell cultures

Vitality test

It is applied to yeast cultures of the Saccharomyces type, such as *Saccharomyces lactis, Saccharomyces fragilis* or the like.

The test gives a quantitative measure of the number of dead cells present in the fermentation.

Experimental method

The cell sample to be tested is mixed with a mixture containing $10^{-4}$ of Trypan Blue together with, for every liter, 0.1 g of $NaN_3$, 6.8 g of $KH_2PO_4$ adjusted to pH 7.2 with KOH, and 8.76 g of NaCl. $CoCl_2$ is added to a final concentration of $10^{-2}$ M in the presence of an equal concentration of EDTA. The mixture is stirred for a few minutes, and then measured with the apparatus heretofore described.

The sample is irradiated in a 2 mm cell using the pulsed laser at $\lambda = 659$ nm, and the absorption variations at $\lambda = 405$ and 435 nm are observed after 1 $\mu$s of delay from the laser pulse. Calibration is necessary in order to gauge the observed amplitude against the amplitude of the laser pulse, the optical alignment etc. For this purpose a suspension is used in which the yeast cells are counted and then all killed by boiling for a few minutes.

Results

Figure 2:
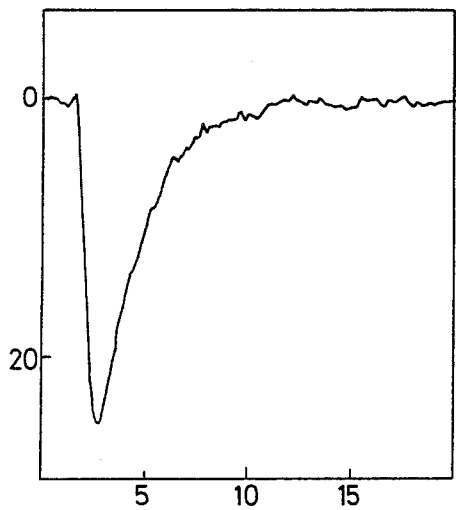

In FIG. 2, the ordinate represents the transient absorption (in mV) observed at $\lambda = 435$ nm when a suspension containing partly killed *Saccharomyces lactis* cells and Trypan Blue is subjected to pulse radiation at $\lambda = 659$ nm as described heretofore. The abscissa represents the time in microseconds ($\mu$s).

Figure 3:
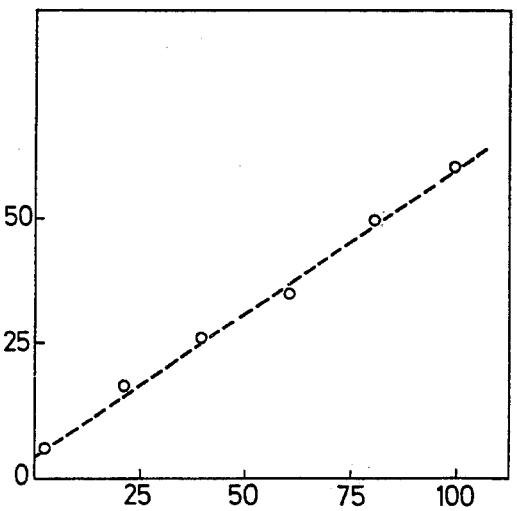

In FIG. 3, the ordinate represents the transient amplitude (in mV) observed after 1 $\mu$s from the beginning of the laser pulse. The abscissa represents the percentage of dead cells in the suspension read by conventional means, i.e. by optical microscope counting.

The correlation is very good, and enables the number of dead cells to be automatically measured in just a few seconds. The sensitivity obtainable can vary around 100–1000 cells/mm$^3$, i.e. less than 1% of the total population present in the broth.

EXAMPLE 2

Testing of cell cultures

Contamination by various strains

The same composition as used for the reaction mixture of Example 1, containing Trypan Blue, enables various types of cells in a fermentation to be distinguished. For two different yeasts of the Saccharomyces type, the transient observed at $\lambda = 435$ nm has a different variation with time, for example the halving time (i.e. the time during which the transient amplitude is reduced by a factor of 2) is 2.3 $\mu$s for *Saccharomyces lactis*, and 1.7 $\mu$s for *Saccharomyces fragilis*.

No transient is observed in dead bacteria cells of the Arthrobacter type. The method is therefore suitable for testing yeast contamination in bacteria cultures, or for distinguishing different yeasts. For this purpose, the sample to be analysed is taken, all the cells present are killed by boiling for a few minutes, the sample is then treated with the mixture containing the dye, and measurements are then made of the amplitude and the decay time of the transient recorded at $\lambda = 435$ nm, when the sample is irradiated with pulses of $\lambda = 650$ nm.

EXAMPLE 3

Measurement of the DNA quantity present in tissues

The method is suitable for quantitatively measuring nucleic acids present in human cells. White blood cells in various compositions were used for this test.

Samples containing various cells with easily measurable quantities of DNA are obtained from eparinised human blood by known methods comprising centrifuging in a Ficoll gradient. A linear Ficoll gradient from 18% to 15% is used, the cells stratified on the gradient are centrifuged for five minutes at $50 \times g$ and for seven minutes at $250 \times g$. Various bands are obtained which when purified contain lymphocytes, monocytes and granulocytes, with small quantities of red corpuscles. The white cells thus obtained are counted and analysed on strips by a microscope using the usual methods. This enables a quantitative evaluation to be made of the DNA contained in the sample, as the average content of chromatin in each type of cell is known.

The various fractions obtained are dyed both separately and mixed together in known proportions.

In order to dye them, the cells are centrifuged and suspended in a solution containing $5 \times 10^{-5}$ M of Acridine Orange in a physiological solution containing 0.05 M of a phosphate buffer at pH 7.2, and also containing $10^{-2}$ M of $CoCl_2$ and $10^{-2}$ M of EDTA.

The suspension obtained is pulse-irradiated using the apparatus described heretofore at a wavelength between $\lambda = 473$ and $\lambda = 532$ nm. It is observed with continuous light at $\lambda = 435$ nm.

The same procedure is followed for a sample containing the same reagents but without the dye. This latter operation is necessary because small quantities of carboxyhaemoglobin present could contribute to the transient absorption.

Figure 4:
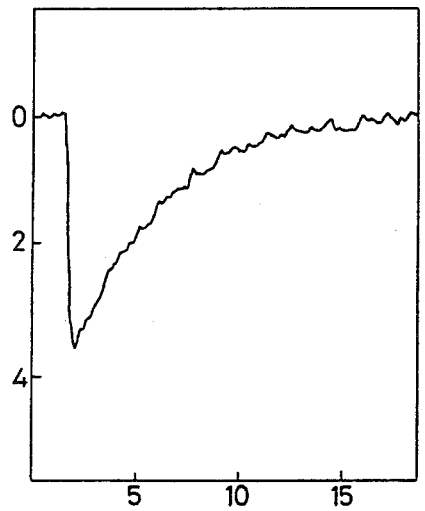

The transient obtained using the sample without the dye is subtracted from that obtained with the complete mixtures, to give the result shown in FIG. 4.

The ordinate represents the amplitude of the transient (in mV), and the abscissa represents the time in $\mu s$.

The variation of the transient absorption is observed at $\lambda = 435$ nm when irradiating a suspension containing human granulocytes and Acridine Orange at $\lambda = 532$ nm, as heretofore described.

Figure 5:
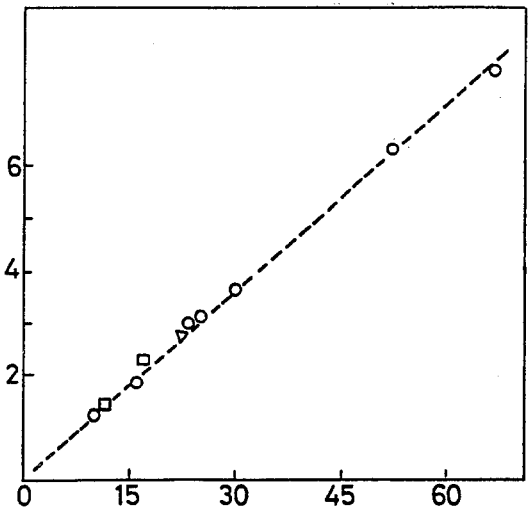

The amplitude of the pulse 1 $\mu s$ after irradiation with the laser is proportional to the DNA content of the sample as shown in FIG. 5. In this figure, the amplitude of the transient (in mV) is shown as a function of the DNA content (expressed as mg/l) for various types of cells, namely lymphocytes and monocytes in various proportions, or monocytes alone, or granulocytes alone, or all leucocytes. The samples contain variable quantities of erythrocytes, and originate from various donors.

The fact that this proportionality is obtained for various contents of different cells taken from various individuals makes it probable that the method can be also reliably applied to biological tissues of other origin, such as epithelial tissues etc.

The measurement of the DNA content together with the measurement of the number of cells present in the tissue could be important in the early diagnosis of cancerous states.

EXAMPLE 4

Characterization of leucocytes in human blood

It is applied to samples of blood which has been rendered non-clotting.

It provides a quantitative evaluation of the total number of leucocytes and of the number of granulocytes, monocytes and lymphocytes.

Experimental method

To a sample of venous human blood which has been rendered non-clotting with heparin in a concentration 0.1 to 0.2 mg/ml of blood, or with sodium EDTA in concentration of 1 mg/ml, there is added a 3.5% soln. of dextran (mol wt 250,000) until having a final concentration of 1.5%, the mixture being then kept in a thermostat at 37° C. for 20 mins. The supernatant liquor is removed, which contains the white-series cells and about 1% of the red cells, and dist. water is added so as to lower the saline concentration to 0.25°/$_{oo}$ (per thousand). After exactly 30 seconds, isotonic character is restored by adding 3.5°/$_{oo}$ aqueous NaCl. The cells are collected by centrifuging at 400. g (gravity pull) for 5 mins. and are then slurried in aqueous 0.9% NaCl or phosphate buffer, pH 7.1, 0.1 M in such a volume that the number of lymphocytes be about 8,000 per cubic millimeter. The recovery of the leucocytes is about 95% with a percentage composition which cannot be distinguished from that of blood: the red cells which remain are in a ratio of about 1:1 with the white cells. The measurements are made on 200 microliters of a cells suspension, in a cell having 2 mm-optical path to which dyestuff and a quencher are added: the cells can be fixed beforehand.

More particularly, the following dyeing techniquies have been used.

To the cell suspension there is added the $CoCl_2$-EDTA quencher plus Brilliant Green in a final concn. $10^{-2}$ and $9.10^{-4}$ M, respectively. Another dyeing technique is to fix the cells with ethanol at a final concentration of 12°/$_{oo}$ (per thousand). After one minute, there is added $CoCl_2$-EDTA and Brilliant Cresyl Blue in the final concn. $10^{-2}$ and $5.10^{-5}$ M, respectively. A third dyeing method which proved useful is like the second described here, but the dyestuff is Nile Blue at $8.10^{-5}$ M.

The samples thus obtained are subsequently irradiated with the pulse laser system described in the introductory part of this specification, at $\lambda = 659$ nm, and are observed with monochromatic light at $\lambda = 435$ nm and $\lambda = 547$ nm, subsequently.

With two different dyeing techniques there can thus be obtained four different transients the characteristics of which are such as to be correlated with the magnitudes to be measured.

Results

Figure 6:
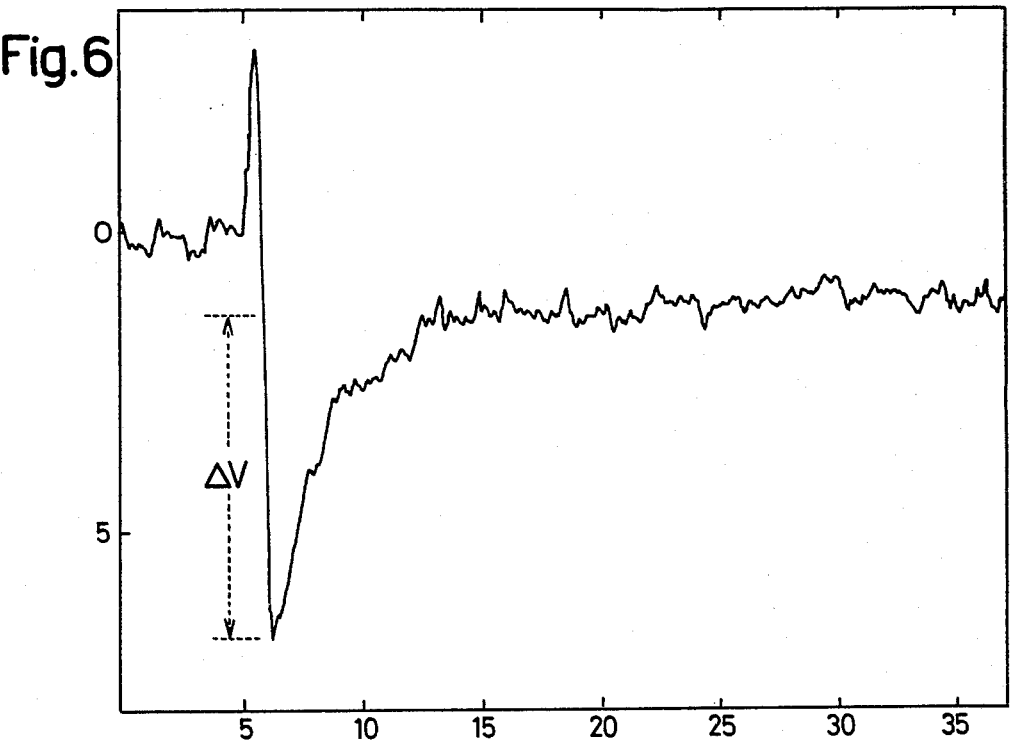
Figure 7:
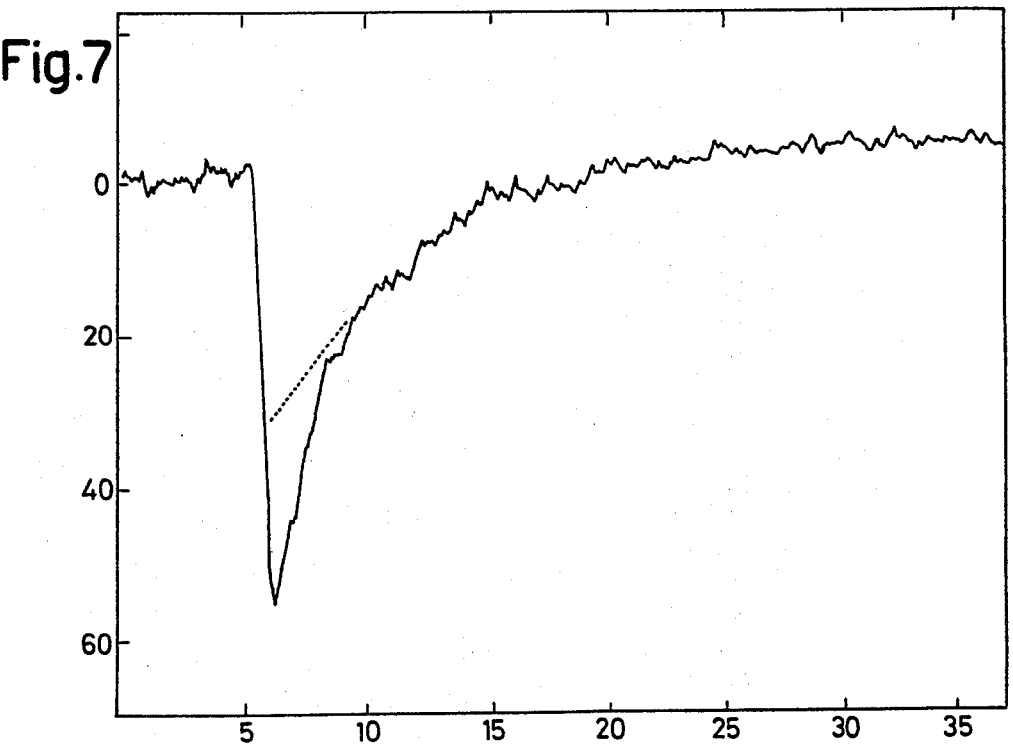

The observation of the thusly treated blood samples is correlated with that obtained with the conventional methods, that is, with the microscopical observation of streaks of whole blood. In FIGS. 6 and 7 there are reported by way of example a few of such transients. More particularly, FIG. 6 shows the amplitude in mV as observed at $\lambda = 547$ nm in the sample dyed with Brilliant Cresyl Blue and fixed with ethanol: the abscissae report the time in microsec. The amplitude, $\Delta V$, as measured as in the Figure between the peak and the value after long times is proportional to the total number of monocytes. It should be noted that in this example, it is essential the presence of Co-EDTA in order to determine the disappearance of the signals coming from other cells or from the free dyestuffs. FIG. 7 reports the transient as observed at $\lambda = 435$ nm in the sample dyed with Brilliant Green (the ordinates are in mV and the abscissae in microsec. as in the previous case). The width of the step, corresponding to the excitation of the triplet state of the dyestuff, presumably bonded to the cellular nucleus as observed on the microscope, can be well correlated with the total number of leucocytes.

The trend of the decay is, in addition, biphasic, as seen in the drawing. The quick stage which is conveniently measured both at $\lambda=435$ nm at $\lambda=547$ nm is, finally, proportional to the number of lymphocytes. Thus, there have been determined all the three independent parameters (number of lymphocytes (l), number of monocytes (m) and number of granulocytes (g), the total number of leucocytes (n), equalling the sum of the three, that is $n=l+m+g$. It should be noted that only a small fraction of the information contained in the tracing as recorded for the observed transients has been utilized for these determinations and one has available the independent observation of the times of decay of the triplet stages and the ratios between the amplitudes at different values of $\lambda$, to effect checks of other nature, such as for example to indicate the presence of pathological cells.

We claim:

1. A method for testing biological tissues and/or liquids, consisting essentially of contacting biological tissue and/or liquid with a composition consisting essentially of a mixture of:
   (a) a dye at a concentration of between $10^{-5}$ and $10^{-4}$ M and chosen from the xanthene, axine, oxazine or acridine series, or from water-soluble dyes of the "diazo" series, or triphenylmethane,
   (b) a medium compatible with said biological tissue and/or liquid, and
   (c) a quencher substance which may be potassium iodide, sodium iodide or the salt of a paramagnetic transition metal and which is capable of de-energising the dye molecules when it encounters them said quencher substance being present in said mixture at a concentration of from $10^{-2}$ to 0.2 M, subjecting the so-treated biological tissue and/or liquid to radiation by a first beam of pulsated light, passing a second beam of monochromatic light through the biological tissue and/or liquid thus treated, and analysing the optical intensity of said second beam as a function of time after it has passed through said biological tissue and/or liquid.

* * * * *